United States Patent [19]

Toms, II

[11] Patent Number: 4,542,472

[45] Date of Patent: Sep. 17, 1985

[54] METHODS AND APPARATUS FOR SURVEYING ROOF MOISTURE CONTENT

[75] Inventor: Thomas M. Toms, II, Raleigh, N.C.

[73] Assignee: Troxler Electronic Laboratories, Inc., Research Triangle Park, N.C.

[21] Appl. No.: 346,171

[22] Filed: Feb. 5, 1982

[51] Int. Cl.$^4$ .......................... G01N 22/04; G01T 3/00
[52] U.S. Cl. .................................. 364/556; 250/390; 364/527; 364/550
[58] Field of Search ............... 364/506, 527, 556, 497, 364/550, 140, 142, 709; 250/390, 391, 392, 473.1; 73/73; 340/600, 601; 324/61 R

[56] References Cited

U.S. PATENT DOCUMENTS

| | | | |
|---|---|---|---|
| 3,492,479 | 1/1970 | Lowery et al. | 250/390 |
| 3,544,793 | 12/1970 | Bless et al. | 250/390 X |
| 3,955,087 | 5/1976 | Ashe | 250/390 X |
| 3,967,197 | 6/1976 | Anderson | 324/61 R |
| 3,976,975 | 8/1976 | Cochran | 364/709 X |
| 4,090,247 | 5/1978 | Martin | 364/709 X |
| 4,217,497 | 8/1980 | Daniels et al. | 250/390 X |
| 4,362,939 | 12/1982 | Horiuchi et al. | 250/390 |
| 4,400,783 | 8/1983 | Locke, Jr. et al. | 364/550 X |

Primary Examiner—Errol A. Krass
Assistant Examiner—Kevin J. Teska
Attorney, Agent, or Firm—Bell, Seltzer, Park & Gibson

[57] ABSTRACT

A method, and a nuclear radiation gauge, for surveying a roof for moisture in which a thermal neutron gauge is positioned at a predetermined location on a roof, the signal representative of the hydrogen content of the roof at that location is generated and registered in a programmable memory device, and the gauge is then moved to a succession of predetermined locations arranged in a predetermined array on the roof while repeating the steps of generating and registering signals at each location.

13 Claims, 5 Drawing Figures

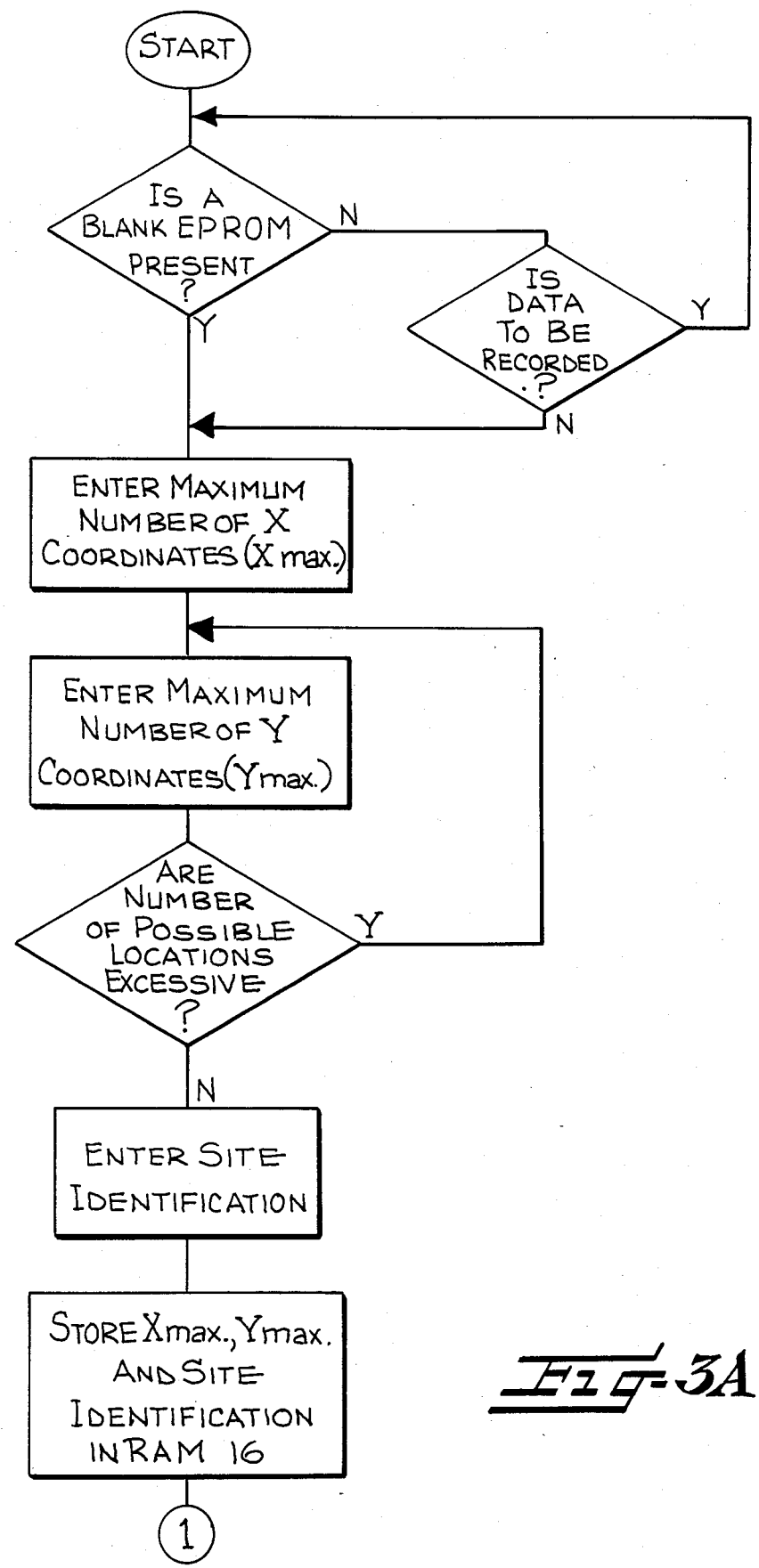

METHODS AND APPARATUS FOR SURVEYING ROOF MOISTURE CONTENT

FIELD AND BACKGROUND OF INVENTION

It has been proposed heretofore that nuclear radiation gauges be employed for measuring physical characteristics of materials. One specific example is the use of nuclear radiation moisture gauges to measure hydrogen content and to relate such measurements to moisture. In surveying an area for variations in a physical characteristic such as hydrogen content and moisture, typical processes involve defining a grid to be applied to the area to be surveyed, then moving a gauge from point to point in the grid while measuring the physical characteristic and noting the gauge reading, and thereafter performing necessary calculations and mapping from field notes. One particular application in which such proposals have met with some success is in the surveying of building roof structures as an approach to determining specific areas to be repaired. In such applications, readings are made at a number of predetermined locations distributed in a predetermined array throughout the area of the roof.

While such surveying practices have achieved some acceptance, the practices are subject to operator error and are time-consuming. As a consequence, access to the result of a survey conducted using a nuclear radiation gauge and as described above is delayed.

BRIEF DESCRIPTION OF INVENTION

With the aforementioned difficulties and deficiencies of prior methods and apparatus particularly in mind, it is an object of the present invention to survey a roof structure for moisture content by measuring the hydrogen content at a predetermined location within an area being surveyed while generating a digital signal representative of the moisture content, registering the generated signal in a programmable memory device, and repeating the steps of measuring while generating and registering at successive locations distributed in a predetermined array throughout the area. By registering generated signals in a programmable memory device, an operator may move quickly from location to location, minimizing the time required to conduct the survey. Additionally, the possibility of operator error is significantly reduced or entirely eliminated.

Yet a further object of this invention is to map the hydrogen content of a roof structure by conducting a survey as briefly described above using a nuclear radiation moisture gauge and thereafter retrieving registered signals from a programmable memory device while processing the registered signals and generating from the processed signals a map display of the area surveyed and the moisture at each location. It is contemplated by the present invention that such retrieval, processing and generating of a display may be accomplished through the use of a digital computer, thereby expediting access to the result of the survey while decreasing or entirely eliminating the possibility of operator error.

Yet a further object of the present invention is to provide, for use by an appropriately trained operator, a nuclear radiation moisture gauge for surveying the moisture content of an area such as a roof. In accordance with the present invention, the gauge incorporates a neutron source, one or more neutron detectors, and signal registering and storing circuitry operatively connected with the detectors for registering a signal representative of moisture content at a location and storing registered signals in a programmable memory device. A central processor unit, forming a portion of the signal registering and storing circuitry, directs the registering and storing of signals and the actions of an operator. By the provision of a gauge as contemplated by the present invention, surveying is simplified for an operator in that the operator need only move from location to location in a predetermined array and as directed, positioning the gauge at each location, and awaiting completion of a gauge-determined time interval for measurement at each location. The operator of the gauge in accordance with the present invention is relieved of the necessity of maintaining field notes of each reading as the readings are taken.

BRIEF DESCRIPTION OF DRAWINGS

Some of the objects of the invention having been stated, other objects will appear as the description proceeds, when taken in connection with the accompanying drawings, in which:

FIGS. 3A–3C are a flowchart illustrating a method for surveying roof moisture content in accordance with the invention.

DETAILED DESCRIPTION OF INVENTION

Figure 1:
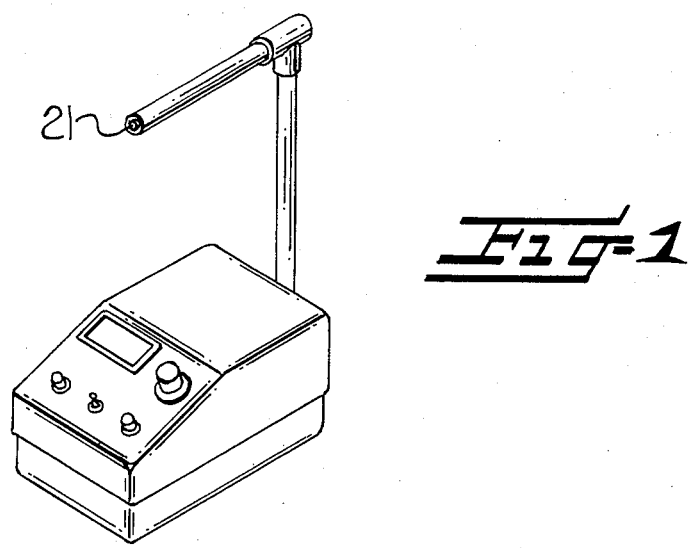
FIG. 1 is a perspective view of a gauge embodying the present invention.
Figure 2:
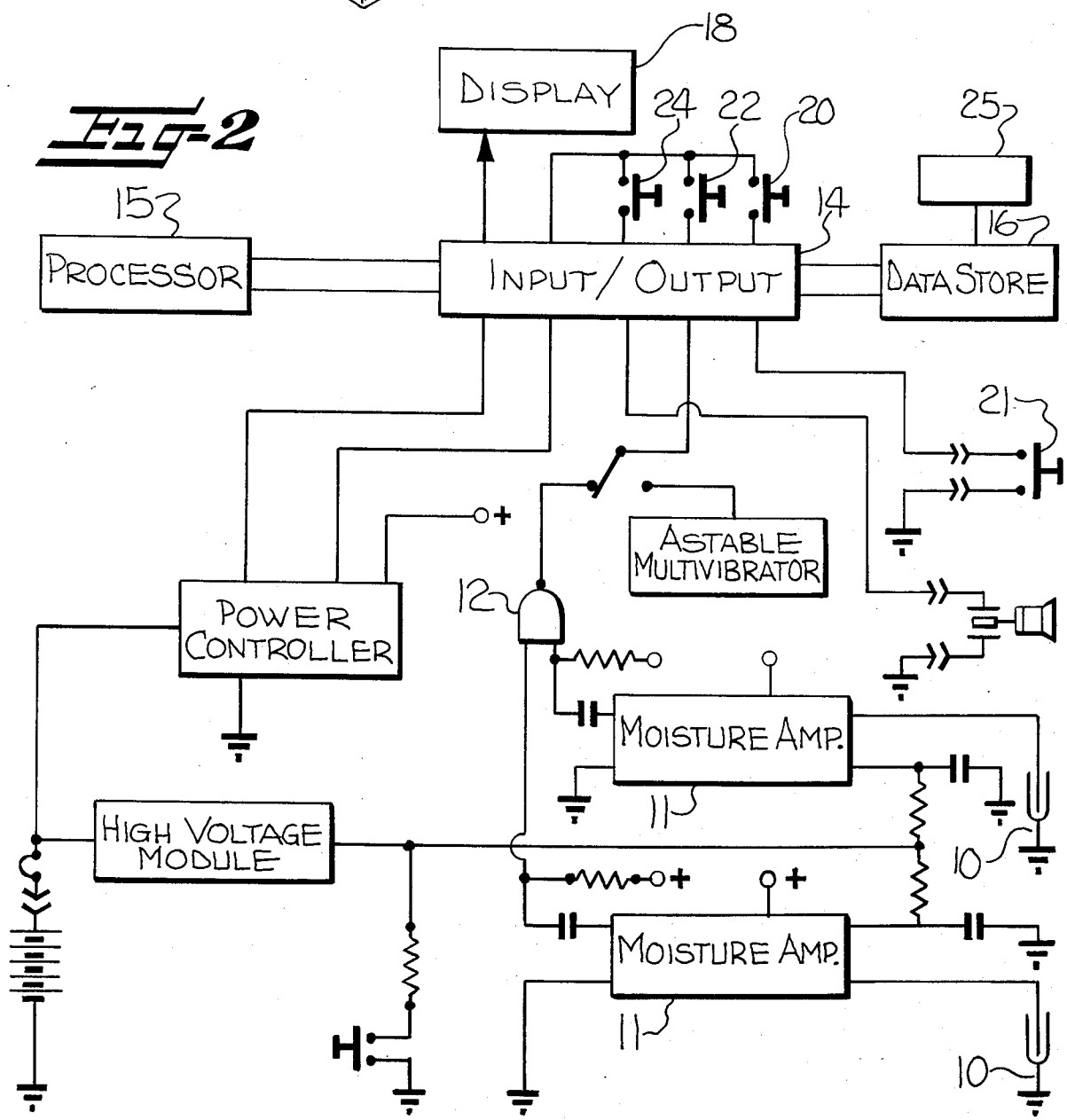
FIG. 2 is a schematic representation of components of the gauge of FIG. 1.

While the present invention will be described more fully hereinafter with reference to the accompanying drawings, in which a preferred embodiment of the present invention is shown, it is to be understood at the outset of the description which follows that persons of skill in the appropriate arts may modify the invention here described while still achieving the favorable results of this invention. Accordingly, the description which follows is to be understood as being a broad, teaching disclosure directed to persons of skill in the appropriate arts, and not as limiting upon the present invention.

The gauge of the present invention may comprise a case containing electronic modules, detector tubes, rechargeable battery packs, and a radioactive source. As is known to persons familiar with such gauges and skilled in their use, a handle is provided to permit an operator to manipulate the gauge so as to position the gauge at successive locations distributed in a predetermined array throughout an area to be surveyed, such as a roof. The nuclear radiation source means will be selected for emitting nuclear radiation of a type which is susceptible to modification by the physical characteristic for which the area is to be surveyed. In the specific instance of a gauge for surveying an area such as a roof for moisture, the radioactive source used in the gauge is a source of fast neutrons, preferably formed of Americium-241 and Beryllium. Such a radioactive source emits fast neutrons which are moderated or slowed by hydrogen atoms in water and become thermal or slow neutrons. As is known to persons skilled in the arts related to nuclear radiation gauges, thermal neutrons may be detected by an appropriate detector means, with the relative geometry of the neutron source and the thermal neutron detector providing particular patterns of response for a particular gauge. Inasmuch as it is contemplated that a person of appropriate skill in the designated arts may determine and select appropriate sources, detectors and geometries, the present description will not set forth specific details of such choices and arrangements.

The present invention contemplates that the gauge may include signal registering and storing means operatively connected with the detector means and responsive thereto for accomplishing several functions in accordance with the present invention. In the specific application here described in detail, signals generated by the thermal neutron detector means 10 are received and amplified by corresponding moisture amplifiers 11 and then gated through a gate device 12 for delivery to input/output circuitry generally indicated at 14. The input/output circuitry 14 serves to coordinate the functions of a number of other components of the gauge in accordance with the present invention, including a central processing unit 15, a data store unit 16, and a display 18.

The input/output circuitry 14 is connected with a start switch 20 which may be mounted on the instrument case and with a remote start switch 21 which may be mounted on a handle for ready manipulation by an operator. Additionally, the input/output circuitry is connected with an increment switch 22 and a decrement switch 24, the functions of which are described more fully hereinafter.

The data store circuitry 16 is operatively connected with a socket 25 for removably retaining a memory storage device of the type known as an Erasable Programmable Read-Only Memory or EPROM, and the data store circuitry 16 includes the circuitry needed for transferring data into the EPROM. As known to persons skilled in the arts of memory devices, an EPROM is a device which may be erased by exposure to ultraviolet light or the like and may thereafter have digital data entered thereinto. In the present invention, the EPROM provides a means for registering signals and thereafter, by removing and transporting the EPROM only, retrieving the registered signals at a remote location at which a central processing unit may process the registered signals and generate from the processed signals a map display of the area surveyed and the physical characteristic properties at each location.

The display 18, in the form preferred, takes the form of a liquid crystal display which is capable of presenting a range of information under the control of the processor 15 and through the input/output circuits 14.

Figure 3B:
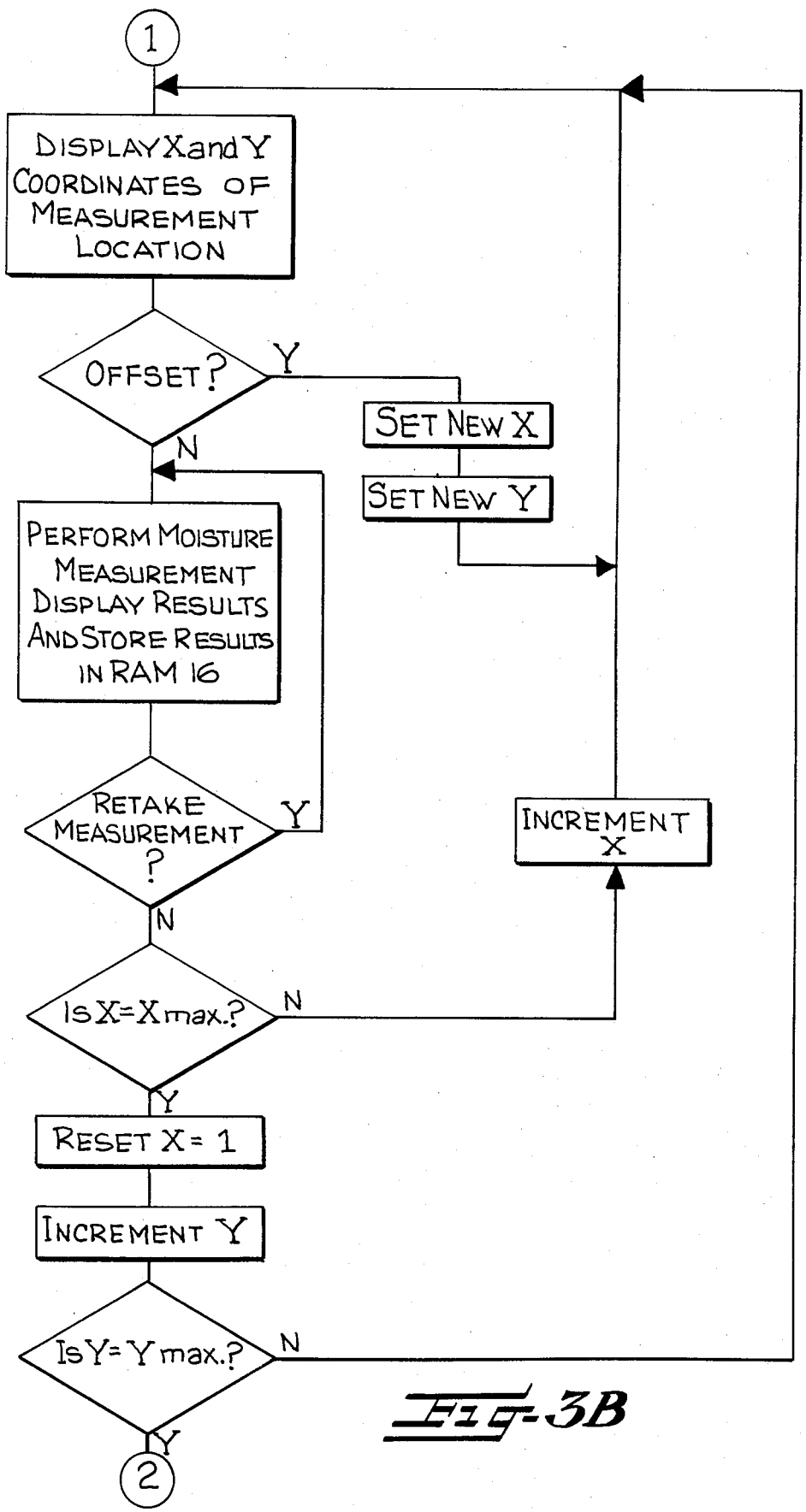
Figure 3C:
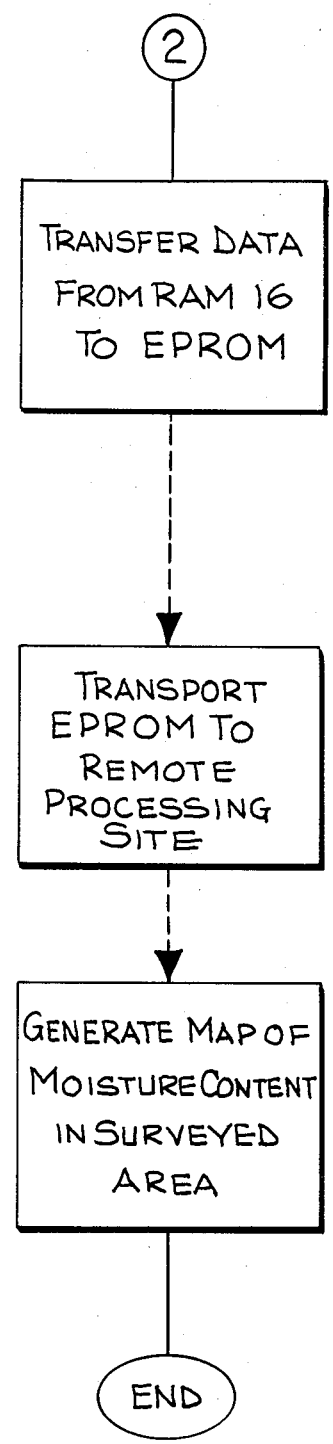

In gauges in accordance with the present invention, the processor circuitry 15 performs a variety of functions, a number of which will now be described in connection with FIGS. 3A-3C. It is assumed that an area to be surveyed is available and that the gauge has been turned on, and a desired time interval for each measurement selected. Upon an operator first pressing the start button, the processor 15 will determine whether or not a blank EPROM is present in the socket 25. If a blank EPROM is present, then the gauge will display on the display 18 an inquiry asking for the coordinates of the area to be surveyed. Coordinates are specified as X and Y coordinates and are for a grid having a number of locations beginning from $X=1$ and $Y=1$ and continuing to such numbers as are required for the area to be surveyed. As will be appreciated, such a $(X, Y)=(n, n)$ coordinate system may extend to such a number of specific locations as may be accommodated in the specific memory devices chosen. Thus, the selection of limits upon the coordinates may be left to the person of appropriate skill in the applicable arts. In an operating model of a gauge in accordance with the present invention, the maximum number allowed for either maximum X or maximum Y is 999 and the number of available memory locations is 3961.

Should the processor circuitry 15 discover that no EPROM is present in the socket 25, then an inquiry will be displayed on the display 18 asking if data is to be recorded. A "yes" response would require the insertion of a blank PROM into the socket 25 before the processor circuitry 15 would permit the operation to continue. A "no" response would permit the programming within the processor 15 to continue, due to an indication of operator awareness that data will not be transferred into an EPROM. The operator may suitably indicate a yes or no response by depressing an appropriate switch provided on the instrument. For example, a positive (yes) response may be indicated by depressing the increment switch 22 and a negative (no) response by depressing the decrement switch 24.

Upon the gauge reaching the programming point of asking for a maximum value of X, by either programming path described above, the operator must then enter a maximum value of X for the predetermined array of predetermined locations in the area to be surveyed. Such a value is entered by holding down the increment switch 24 until such time as the display 18 displays the appropriate number. The decrement switch 22 operates in a similar fashion, should there be an incorrect display. When the operator has manipulated the gauge so that the display 18 presents the selected number, an actuation of the start button will cause the programming of the processor to retain the maximum value of X and display an inquiry concerning the maximum value of Y. The maximum value for Y is then similarly entered. Following entry of the maximum Y value, the processor 15 will calculate the number of possible locations against the number of locations available in the data store circuitry 16 and, if the number is excessive, display a request that the operator select different values for X and Y. If the product of the maximum X and maximum Y numbers does not exceed available memory, then the gauge will ask for a site identification number. Such a site identification number is for user information only and will permit subsequent correlation of the registered signals in the programmable memory device with the specific area or roof which has been surveyed.

Upon the next operation of the start switch 20, 21, the site identification number and the maximum X and maximum Y values are stored in a Random Access Memory (RAM) in the data storage circuitry 16 and the processor circuitry 15 through the display 18 indicates the coordinates of the first predetermined location at which the physical characteristic is to be measured. That is, the display 18 would indicate 1, 1. The operator is then to position the gauge at location 1, 1, and initiate the step of measuring the moisture in the roof at that point by closing a start switch 20, 21. As measurement continues, a digital signal representative of the measured characteristic is generated within the circuitry of the gauge and, under the control of programming steps performed within the processor 15, entered into the RAM in the data storage circuitry 16 and displayed on the display 18. The detection and counting of thermal neutrons, together with the calculation of moisture data from measured counts, are believed within the understanding of persons appropriately skilled in the applicable arts and will not here be discussed in great detail.

Upon completion of the measurement and registration of the generated signal in the RAM, the processor 15 through the display 18 will indicate that data is to be taken from another location. In an operating embodiment of a gauge in accordance with the present invention, the coordinates are incremented in the X direction first, so that the indicated second location would be (2, 1). The programming operative within the processor 15 will attend to the successive locations at which the steps of measuring, generating and registering occur, so as to build a file of the data in an orderly manner.

Upon occasion, when surveying an area, it may become necessary to avoid an obstacle. Should that occur, the programming operative within the processor 15 will accommodate deletion of a specific location. By signaling through the input/output circuitry 14 to the processor 15, an X or Y coordinate offset may be indicated. Through use of the increment switch 24 and decrement switch 22, the indicated value for one or both of the coordinate locations (X, Y)=(n, n) may be modified so as to reestablish a proper location in the array on an alternate side of the obstacle. In an operating embodiment of the present invention, the programming within the processor 15 assumes that the operator wishes only to avoid an obstacle, and will not permit resumption of measuring, generating and registering a generated signal until such time as normal gauge operation has been restored by appropriate signals.

The programming operable within the processor 15 may additionally provide for insertion of a newly generated signal with respect to a specific location. With such operation, any questionable signal generated during the course of a survey may be replaced. In such a sequence, programming within the processor 15 may be entered in a manner similar to that provided for avoiding an obstacle, while indicating that the move is not to a new location. An indication that the move is not to a new location will be followed by a displayed inquiry from the processor 15 as to whether new data is to be registered. A signaled affirmative or yes will permit use of the increment switch 24 and decrement switch 22 to identify the specific location at which the registering of a previously generated signal is to be replaced by the registering of a newly generated signal. Measurement at the specifically identified location may then be completed.

As will be noted from the discussion given above, the step of registering a generated signal in a programmable memory device, in accordance with the present invention, comprises first filing the generated signals in RAM. As the survey of an area is completed, the file built by registering the signals in RAM may be transferred under the control of the processor 15 into the EPROM, which is a discrete, separable memory device. Once transferred, the file of signals will be retained by the EPROM indefinitely, until such time as the EPROM is erased through the use of ultraviolet light or as otherwise provided for the particular device chosen. The file generated can be closed at any time, by signaling to the processor 15 that the end of the file has been reached.

Thereafter, if appropriate, the discrete, separable memory device provided by the EPROM may be removed from the gauge and transported from the area surveyed to a remote area at which the file of registered signals retained within the EPROM may be retrieved and processed. With such retrieval and processing, and particularly with the use of computers equipped with plotters as peripheral devices, a directly readable map having areas identified by the moisture content found within the areas may be plotted, in a manner which will be appreciated by persons with appropriate skill in the applicable computer technology arts. Alternatively, numerical measurement values may be entered and displayed graphically at the specific locations in the array.

When used as described hereinabove, the programmable memory within the gauge of the present invention accomplishes the function of transmitting data from the site of original data generation to a remote location for retrieval and processing by means of a separable memory device as provided by the EPROM. In accomplishing such function, it will be understood that the devices used for separable memory devices need not be restricted to EPROMs as described, but may take the form of electrically erasable programmable read-only memories or such other memory devices as are known to and available to persons of appropriate skill in the applicable arts. Further, transmission of the file of generated signals by the use of a discrete, separable memory device is contemplated as being one specific form of transmission available. It is additionally contemplated that provision may be made for direct connection, such as by engagement with the socket provided for the EPROM, with a data communicating interface device which would make possible the transmission of data from the RAM through other available communication media such as telephone lines. Thus, the retrieval of registered signals from the programmable memory is contemplated as including transmittal of the filed, generated signals from the RAM essentially directly to a processing computer unit which may be at a remote location.

In the drawings and specification, there has been set forth a preferred embodiment of the invention, and although specific terms are employed, they are used in a generic and descriptive sense only and not for purposes of limitation.

That which is claimed is:

1. A nuclear radiation gauge for surveying a roof for moisture content at a plurality of measurement locations arranged in a predetermined array on the roof, said gauge comprising:

neutron source means for emitting fast neutrons, thermal neutron detector means mounted in predetermined spaced relation to said source means for detecting neutrons emitted from said source means which have been moderated and slowed by hydrogen atoms and for generating signals representative of the moisture at a location at which the gauge is positioned on the roof, signal registering and storing means connected with said detector means and responsive to generated signals for registering a signal representative of the moisture at a location at which the gauge is positioned on the roof, said signal registering and storing means including a programmable memory means for storing registered signals generated at a succession of locations at which the gauge is successively positioned, and processor means operatively connected with said signal registering and storing means for responding to the registration of a generated signal in a programmable memory device by generating the coordinates indicative of the next successive location distributed in the predetermined array and at which the gauge is to be positioned.

2. A gauge according to claim 1 wherein said signal registering and storing means comprises a discrete, separable memory device for storing a file of registered signals generated at a succession of locations at which the gauge is successively positioned, said separable memory device being removable from said gauge for subsequent retrieval and processing of the registered signals at a remote location.

3. A gauge according to claim 1 wherein said processor means is for selectively overriding an indicated and displayed location selection while identifying in the programmable memory means an alternative predetermined location at which the gauge is positioned.

4. A gauge according to claim 1 wherein said processor means is for identifying a specific location at which the registration of a previously generated signal is to be replaced by the registering of a newly generated signal upon the gauge being positioned at the identified specific location.

5. A method of surveying a roof for moisture with the use of a thermal neutron moisture gauge having a programmable memory device, said method comprising the steps of:
   (a) subdividing the roof area to be mapped into an array consisting of a plurality of measurement locations,
   (b) placing a thermal neutron moisture gauge at a predetermined location within said array on the roof,
   (c) generating a signal representative of the hydrogen content of the roof at that location and registering the signal in a programmable memory device,
   (d) generating the coordinates of the next successive location within the array at which the step of signal generating and registering is to be repeated and displaying to an operator the coordinates for the next successive location,
   (e) moving the gauge to the indicated next successive location, and
   (f) successively repeating steps b, c, d and e within the predetermined array.

6. A method according to claim 5 further comprising the step of selectively overriding an indicated and displayed location selection and identifying in the programmable memory device an alternative predetermined location at which the steps of generating and registering occur.

7. A method according to claim 5 further comprising the steps of identifying a specific location at which the registering of a previously generated signal is to be replaced by the registering of a newly generated signal, and then repeating the steps of generating and registering the signal at the identified location and registering the newly generated signal in the programmable memory device.

8. A method of mapping moisture in a roof with the use of a thermal neutron moisture gauge having a programmable memory device, said method comprising the steps of:
   (a) subdividing the roof area to be mapped into an array consisting of a plurality of measurement locations,
   (b) storing in the programmable memory device a signal representative of the number of measurement locations in the array,
   (c) placing the thermal neutron moisture gauge at a first predetermined location within said array on the roof,
   (d) generating a signal representative of the hydrogen content of the roof at that location and registering the signal in a programmable memory device,
   (e) successively displaying to the operator the coordinates of the next measurement locations within said array on the roof and at each such successive location repeating the steps of generating a signal representative of the hydrogen content of the roof at that location and registering the signal in the programmable memory device, and thereafter
   (f) retrieving from the programmable memory device the registered signals representing the number of measurement locations and the hydrogen content at the respective measurement locations and processing the retrieved signals in a data processing device remote from the moisture gauge to generate therefrom a map display of the roof and the moisture at each location.

9. A method according to claim 8 wherein the step of registering the generated signal in a programmable memory device comprises filing the generated signals in a first programmable memory device and subsequently transferrring the file to a discrete, separable memory device connected to the first programmable memory device, and further wherein the step of retrieving the registered signals from the Programmable memory includes physically separating the separable memory device from the first programmable memory device and transporting the separable memory device from the area surveyed to a remote area at which the steps of processing the retrieved signals and generating a map display are to be performed.

10. A method according to claim 8 wherein the step of registering the generated signal in a programmable memory device comprises filing the generated signals in a first programmable memory device and further wherein the step of retrieving the registered signals from teh programmable memory comprises transferring the file from the first programmable memory device to a memory device remote from the moisture gauge and at which the steps of processing registered signals and generating a map display are to be performed.

11. A nuclear radiation gauge for surveying a roof for moisture content at a plurality of measurement locations arranged in a predetermined array on the roof, said guage comprising:
   (a) neutron source means for emitting fast neutrons,
   (b) thermal neutron detector means mounted in predetermined spaced relationship to said source means for detecting neutrons emitted from said source means which have been moderated and slowed by hydrogen atoms and for generating signals representative of the moisture at a location at which the gauge is positioned on the roof, and
   (c) signal registering and storing means connected with said detector means and responsive to generated signals for registering a signal representative of the moisture at a location at which the gauge is positioned on the roof,
   said signal registering and storing means including a programmable memory means having,
   means for storing the registered signals generated at each of the successive measurement locations at which the gauge is successively positioned, means for indicating to the programmable memory means the coordinates of a measurement location where an obstruction exists and a measurement thus cannot be made and for identifying in the programmable memory device the coordinates of an alternative measurement location where the measurement is to be made, and means for transferring the stored signals taken from the measurement locations on the roof to a location remote from the moisture gauge for subsequent processing of the registered signals at a remote location.

12. A guage according to claim 11 wherein said means for transferring the stored signals comprises means for filing the stored signals in a separable memory device which is removable from the gauge.

13. A gauge according to claim 11 wherein said signal registering and storing means also includes means for storing along with said registered signals an identification of the particular site of the roof survey.

* * * * *